United States Patent [19]

Lemanski et al.

[11] Patent Number: 4,544,673
[45] Date of Patent: Oct. 1, 1985

[54] PROCESS FOR PRODUCING LOW MOLECULAR WEIGHT HYDROCARBONS FROM CARBON MONOXIDE AND HYDROGEN

[75] Inventors: Michael F. Lemanski, Cleveland; Wayne R. Kliewer, North Randall, both of Ohio

[73] Assignee: Standard Oil Company, Ohio

[21] Appl. No.: 585,746

[22] Filed: Mar. 30, 1984

Related U.S. Application Data

[62] Division of Ser. No. 440,120, Nov. 8, 1982, Pat. No. 4,451,579.

[51] Int. Cl.$^4$ ................................................. C07C 1/04
[52] U.S. Cl. ..................................................... 518/713
[58] Field of Search .......................................... 518/713

[56] References Cited

U.S. PATENT DOCUMENTS 2,960,518  11/1960  Peters ................................. 518/713
4,298,354  11/1981  Hardman et al. .................... 44/56

Primary Examiner—Howard T. Mars
Attorney, Agent, or Firm—David J. Untener; Larry W. Evans

[57] ABSTRACT

Low molecular weight hydrocarbons are produced by contacting carbon monoxide and hydrogen at elevated temperatures and pressures with a catalyst comprising oxides of chromium, molybdenum and/or tungsten, copper, thorium or uranium and at least one alkali or alkaline earth metal. Catalysts are provided which are prepared by the procedure of adding an alkali or alkaline earth metal carbonate to an aqueous solution or slurry containing decomposable salts of thorium or uranium and copper chromate, copper tungstate and/or copper molybdate to form a precipitate. The precipitate is heated, neutralized, dried and thereafter calcined and reduced.

10 Claims, No Drawings

PROCESS FOR PRODUCING LOW MOLECULAR WEIGHT HYDROCARBONS FROM CARBON MONOXIDE AND HYDROGEN

BACKGROUND OF THE INVENTION

This is a division of application Ser. No. 440,120 filed Nov. 8, 1982 now U.S. Pat. No. 4,451,579.

1. Field of the Invention

The present invention relates to a novel catalytic process for producing low molecular weight hydrocarbons from carbon monoxide and hydrogen. More particularly, this invention relates to the production of low molecular weight hydrocarbons from carbon monoxide and hydrogen in the presence of a mixed metal oxide catalyst comprising oxides of chromium, molybdenum and/or tungsten, copper, thorium or uranium and at least one alkali or alkaline earth metal.

2. Description of Art

The production of hydrocarbons from carbon monoxide and hydrogen using mixed oxide catalysts containing Group VIA metals of the Periodic Table have been known for several decades. For example, U.S. Pat. No. 2,726,218 discloses a process for preparing high molecular weight hydrocarbons in the presence of a catalyst containing a tungstite of at least one metal of the class consisting of nickel and cobalt. These tungstites may contain modifiers or promoters such as barium, cadmium, chromium, thorium, cobalt, copper, etc., as desired and may be supported or unsupported.

U.S. Pat. No. 2,183,146 to Michael discloses a process for the production of hydrocarbons and the derivatives containing oxygen from carbon monoxide and hydrogen in the presence of metals of the ion group which have been formed by decomposition of the carbonyl compounds. The activity of these catalysts can be increased by the addition of other compounds such as aluminum oxide and hydroxide or silicon dioxide and also compounds of copper, titanium, manganese, tungsten, molybdenum, chromium, thorium, cerium, zirconium or other rare earths. Small amounts of alkalis or alkaline earths are also taught to be useful therein.

U.S. Pat. No. 4,199,522 to Murchison et al. teaches the production of olefins of two to four carbon atoms from carbon monoxide and hydrogen in the presence of a catalyst having the surface area less than about 100 meters$^2$ gram and contain at least one element from the group consisting of molybdenum, tungsten, rhenium, ruthenium, nickel, paladium, rhodium, osmium, iridium and platinum and at least one material selected from the group consisting of lithium, sodium, potassium, rubidium, cesium, magnesium, calcium, strontium, barium and thorium.

However, a problem encountered with the upgrading of carbon monoxide and hydrogen involves the highly unselective nature of the Fischer-Tropsch reaction mechanism and many of these catalysts are not highly selective for the production of low molecular weight hydrocarbons, often producing excess carbon dioxide. Conversely, the catalyst of the present invention exhibits high selectivities toward the production of low molecular weight hydrocarbons such as $C_1$ to $C_4$ hydrocarbons from carbon monoxide and hydrogen.

SUMMARY OF THE INVENTION

According to this invention, a process is provided for producing low molecular weight hydrocarbons at elevated temperatures and pressures comprising contacting carbon monoxide and hydrogen with a catalyst represented by the empirical formula:

$$[Cu_{0.1-3}(Z)]_{0.1-3}M_{0.1-3}A_{0.01-2}O_x \tag{I}$$

wherein Z is at least one compound selected from the group consisting of oxides of chromium, molybdenum and tungsten; M is selected from the group consisting of thorium and uranium; A is at least one element selected from the group consisting of the alkali and alkaline earth metals; and x is a number which satisfies the valence requirements of the other elements present.

In another embodiment of the present invention, a preferred process for preparing the catalyst of formula (I) is provided.

DETAILED DESCRIPTION OF THE INVENTION

Reactants

The present invention provides a novel catalyst and process for producing low molecular weight hydrocarbons from carbon monoxide and hydrogen containing reactant gases. Although the carbon monoxide and hydrogen required for this process can be obtained from any source, a common carbon monoxide and hydrogen containing gas is known as synthesis gas. Typically, synthesis gas is derived by heating coke in the presence of air and then steam or by the partial combustion of coal, natural gas or petroleum hydrocarbons. The molar ratio of carbon monoxide to hydrogen required for this process ranges generally from at least about 1/0.1 to an upper limit of about 1/5. Preferably, the molar ratio should be about 1/1.

It is desirable to use carbon monoxide and hydrogen containing reactant gases which contain as little sulfur as possible since sulfur is a known poison for copper containing catalysts. Preferably, the reactant gas will be essentially sulfur-free.

Process Conditions

The inventive process can be carried out by contacting the gaseous reactant with the inventive catalyst in either a fluid-bed mode or a fixed-bed mode. The process can also be carried out in continuous or batch operation.

The process conditions can vary widely. Typically, the reaction pressure can vary from about 100 PSIG to about 10,000 PSIG and preferably from 500 PSIG to about 2,000 PSIG. The reaction temperature can range from at least about 200° C. to about 600° C., preferably ranges from about 275° C. to about 500° C. and most preferably from about 300° C. to about 400° C. The contact time of the reactants can also vary widely such as from about 10 seconds to about 500 seconds. However, the contact time is generally below about 300 seconds and is typically about 50 seconds to about 150 seconds. It should be noted that low temperatures and high pressures have been found to be conducive to the production of oxygenates such as alcohols and acids.

Catalyst

The catalyst of the present invention is typically an oxide catalyst, and as illustrated in formula (I), are oxides of chromium, molybdenum and/or tungsten, copper, thorium or uranium and at least one component selected from the alkali and alkaline earth metals.

Although the metals of the oxide catalyst can have varying oxidation states, chromates, molybdates and/or tungstates have been found to be particularly effective Group VIA metal oxides. Chromates, molybdates and tungstates as used herein, define metals of Group VIA of the Periodic Table which are found as metal oxides in their anionic form. These metals characteristically exhibit a common oxidation state of VI. For example, chromate includes chromate and dichromate ions wherein chromium is found in an oxidation state of VI (+6). The chromate ion is typically represented as $CrO_4^{-2}$ while dichromate is represented as $Cr_2O_7^{-2}$. Molybdates and tungstates are anionic tetraoxides and are represented by the general formulas $MoO_4^{-2}$ and $WO_4^{-2}$.

It has been found that the catalysts of the present invention are highly selective to $C_{1-4}$ hydrocarbons and the anonic metal oxide catalysts containing thorium have been found to be particularly selective for $C_1$-$C_4$ alkanes with the production of essentially no alcohols or acids. Although not wanting to be bound to theory, it is believed that the selectivity of the chromate, molybdate and chromate catalyst of the present invention is achieved by the presence of the chromate, molybdate or tungstate anion. More specifically, the Group VIA anion must be stabilized during the catalyst preparation. One technique for achieving this is to introduce the chromate, molybdate or tungstate as copper chromate, copper molybdate or copper tungstate. This allows the chromate, molybdate or tungstate to remain in the introduced state and not change to form other oxides.

The catalysts of the present invention can be prepared by many techniques known to those skilled in the art. However, in a preferred embodiment of the present invention, these catalysts are prepared by a procedure involving adding an alkali or alkaline earth metal carbonate to an aqueous solution or slurry containing decomposable salts of thorium or uranium and copper chromate, copper tungstate and/or copper molybdate to form a precipitate. This precipitate is heated, neutralized, dried and thereafter calcined and reduced.

More specifically, the catalyst of the present invention can be prepared by the following procedure. A solution or slurry, preferably aqueous, containing copper chromate, copper molybdate and/or copper tungstate and decomposable salts of thorium is first formed. Nitrates are preferably used as the decomposable salts, although salts having other decomposable anions such as acetates, propionates, benzoates, acetylacetonates, chlorides and the like can be employed.

To the above solution is added alkali or alkaline earth carbonate, preferably also in the form of an aqueous solution. During this addition, the add mixture is preferably maintained at an elevated temperature, such as 80°-95° C. Addition of alkali or alkaline earth metal carbonate is continued while maintaining the temperature of the system preferably between 80°-95° C. unitl the pH of the system, which is initially at about 1, increases to at least 7.5, preferably at least 8, most preferably 9-10. An alkali or alkaline earth metal hydroxide can also be used in place of the carbonate, although the carbonate is preferred.

The above solution is allowed to digest for several hours while the temperature of the system is maintained at about 80°-95° C. During this time, the reaction mixture volume will reduce to approximately one-half its original volume.

After sufficient digestion, usually when no more color changes are observed, an acid is added to bring the pH to about neutral. Although other acids can be used, preferably nitric acid is employed. The precipitate is then filtered and washed with water until the alkali or alkaline earth metal content of the finished catalyst falls to the desired value. This is easily determined by trial and error.

The precipitate is then dried at a convenient temperature, for example, 120° C., and then calcined for a time and at a temperature sufficient to drive out the remaining water in the precipitate and decompose decomposable ions remaining in the precipitate, such as nitrate and carbonates. Temperatures of about 250°-500° C., preferably 350°-450° C. for periods of 30 minutes to about 2 hours at atmospheric pressures have been found sufficient for this purpose.

It is preferable to reduce the calcined precipitate prior to use in the inventive process since the inventive process utilizes a reducing atmosphere. However, pre-reduction of the catalyst is not necessary since the catalyst will automatically undergo reduction to an equilibrium value during use although the activity of the catalyst will not be as great as when a proper prereduction procedure is carried out. Since a very exothermic reaction may occur when the reducing gas is contacted with the calcined precipitate, it is preferable to subject the calcined precipitate to a controlled reduction procedure in order to avoid heating the calcined precipitate to above about 300° C. It is believed that heating of the calcined precipitate to temperatures above about 300° C. will cause significant reduction of the activity of the ultimate catalyst due to sintering of particles of the calcined precipitate.

The controlled reduction of the calcined precipitate can be carried out in the following manner, although other satisfactory techniques can be employed as well. The calcined precipitate is first heated under inert atmosphere to a temperature of about 200° C. Next, an inert gas containing a low concentration, such as about 5 percent, of a reducing gas, preferably hydrogen although a mixture of hydrogen and carbon monoxide can also be employed, is admitted to the gas surrounding the catalyst for initial reduction of the metal. Thereafter, the concentration of the reducing gas is slowly increased to 100 percent, care being taken to keep the rate of reducing gas applied low enough to prevent the temperature of the catalyst from exceeding the value at which significant sintering occurs, usually about 300° C. After reaching pure hydrogen flow the catalyst is reduced for about 4 hours.

The catalyst of the present invention can be used alone or supported on various inert supports such as silica, alumina, alundum, mullite and the like. These materials are preferably low surface area support and can be added to the catalyst during this preparation or after the preparation of the catalyst in conventional manners.

As mentioned above, it is believed that this preparation is particularly effective due to the presence of the chromate, molybdate and/or tungstate component in the active catalyst. This suprising result was discovered through X-ray diffraction techniques. For example X-ray diffraction patterns for a thorium-copper-tungstate catalyst indicate that the major component in the active catalyst is the copper tungstate although thorium oxide and trace amounts of metal oxides are also present.

SPECIFIC EMBODIMENTS

Catalyst Preparation

Examples 1 and 2

To 600 ml of distilled water were added 72.2 grams of CuWO$_4$ and 84.4 grams of Th(NO$_3$)$_4$·4H$_2$O. The solution was placed in a 1 liter ball mill jar containing milling stones and milled for approximately 16 hours. After milling, the solution was diluted with distilled water until a volume of 800 ml was obtained. The solution was heated to 90° C. and while stirring, a solution of 44.6 grams of Na$_2$CO$_3$ in 800 ml of distilled H$_2$O at 90° C. was added to the stirring reaction mixture. Using a pH meter, sufficient additional Na$_2$CO$_3$ was added to bring the pH slurry to 9.5. The temperature of the solution was maintained at 90° C. for approximately 2 hours allowing digestion. After cooling to room temperature, the pH was adjusted to 7.0 with a 20 percent HNO$_3$ solution. The slurry was filtered using vacuum and sucked as dry as possible. The filtered cake was washed 3 times by re-slurrying in distilled H$_2$O at 60°–80° C. and refiltering. The catalyst was calcined for 16 hours at 350° C. under an air atmosphere. The sodium content of the finished catalyst was approximately 0.1 weight percent. Before loading into the reactor, the calcined catalyst was ground and screened through a U.S. standard No. 10–30 mesh.

The above prepared catalyst was placed in a 40 cc reactor and placed in a reactor oven. Under a nitrogen atmosphere (100 cc/min), the catalyst was heated to 200° C. After reaching 200° C., hydrogen is introduced in addition to the original hydrogen flow at 20 cc/min. After approximately 10–15 minutes, the hydrogen content was slowly increased and the nitrogen flow was slowly reduced. This process continued for approximately 2 hours or until only the hydrogen flow was present at 200 cc/min. After reaching pure hydrogen flow, the catalyst was reduced for 4 hours and then nitrogen was introduced (15 cc/min) and the hydrogen supply was discontinued.

Examples 3 and 4

The procedure of Examples 1 and 2 was followed except that 51.3 grams of CuMoO$_4$ was added in place of the CuWO$_4$. The final catalyst contained about 1.1 weight percent Na.

Examples 5 and 6

The procedure of Examples 1 and 2 were followed except that 76.8 grams of UO$_2$(NO$_3$)$_2$·6H$_2$O was used in place of the Th(NO$_3$)$_2$·4H$_2$O.

Examples 7 and 8

These catalysts were prepared in accordance with Examples 1 and 2 except that 50 grams of potassium, rubidium, lithium and cesium carbonates were added in place of the sodium carbonate of Example 1, respectively.

Hydrocarbon Production

A series of experiments were run in order to determine the catalytic activity of the various catalysts prepared in Examples 1–10 for the production of low molecular weight hydrocarbons. In each experiment, 40 cc of catalyst was charged into a fixed-bed reactor and contacted with CO/H$_2$ in a molar ratio of about 1/1 mixture at a velocity of 555 cc/min for 60 sec at 1500 psig. The process conditions and results are reported in Table I.

TABLE I

| | | | Percent Selectivity for the Conversion of CO and H$_2$ to Hydrocarbons** | | | | | | | | |
|---|---|---|---|---|---|---|---|---|---|---|---|
| | | Temperature | Products | | | | | | | | |
| Example | Catalyst | (0° C.) | CO$_2$ | CH$_4$ | C$_2$ | C$_2$= | C$_3$ | C$_3$= | C$_4$ | C$_4$= | Oxygenates |
| 1 | [Cu(WO$_4$)]$_{1.5}$ThNa$_y$O$_x$ | 275 | 39.10 | 59.42 | — | — | 1.57 | — | — | — | — |
| 2 | [Cu(WO$_4$)]$_{1.5}$ThNa$_y$O$_x$ | 325 | 61.54 | 33.16 | 0.68 | — | 4.62 | — | — | — | — |
| 3 | [Cu(WO$_4$)]$_{1.5}$ThNa$_y$O$_x$ | 275 | 79.03 | 20.97 | — | — | — | — | — | — | — |
| 4 | [Cu(WO$_4$)]$_{1.5}$ThNa$_y$O$_x$ | 325 | 58.55 | 20.45 | 9.39 | — | 4.02 | 4.02 | 3.59 | — | — |
| 5* | [Cu(WO$_4$)]$_{1.5}$UNa$_y$O$_x$ | 275 | 40.40 | 11.90 | 39.90 | — | — | 3.32 | 4.43 | — | — |
| 6* | [Cu(WO$_4$)]$_{1.5}$UNa$_y$O$_x$ | 325 | 50.60 | 22.00 | 10.70 | — | 10.10 | — | 5.10 | — | 2.1 |
| 7 | [Cu(WO$_4$)]$_{1.5}$ThK$_y$O$_x$ | 325 | 51.25 | 33.43 | 10.03 | — | 4.18 | — | 1.11 | — | — |
| 8 | [Cu(WO$_4$)]$_{1.5}$ThRb$_y$O$_x$ | 325 | 53.56 | 26.92 | 9.31 | — | 6.57 | — | 3.05 | — | — |
| 9 | [Cu(WO$_4$)]$_{1.5}$ThLi$_y$O$_x$ | 325 | 59.18 | 34.01 | — | — | 4.08 | — | 2.72 | — | — |
| 10 | [Cu(WO$_4$)]$_{1.5}$ThCs$_y$O$_x$ | 325 | 51.54 | 29.07 | 10.67 | — | 5.90 | — | 2.81 | — | — |

*The pressure was 750 psig.
**Selectivity is based on percent carbon utilized
y is between about 0.01–2

As shown in the above table, the catalysts of the present invention show high selectivities for the production of low molecular weight hydrocarbons from carbon monoxide and hydrogen. Further, the thorium catalyst prepared by the preferred method of preparing the catalysts is highly selective for C$_{1-4}$ alkanes with the production of essentially no alcohols or acids.

Thus it should be apparent to those skilled in the art that the present invention accomplishes the objects set forth above. It is to be understood that the present invention is not to be limited by the examples set forth herein which have been provided merely to demonstrate operability. The scope of this invention includes equivalent embodiments, modifications and variations that fall within the scope of the attached claims.

What is claimed is:

1. A process for producing low molecular weight hydrocarbons at elevated temperatures and pressures comprising contacting carbon monoxide and hydrogen with a catalyst represented by the formula:

$$[Cu_{0.1-3}(Z)]_{0.1-3}M_{0.1-3}A_{0.01-2}O_x$$

wherein
- Z is tungstate; 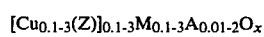
- M is selected from the group consisting of thorium and uranium;

A is at least one element selected from the group consisting of the alkali and alkaline earth metals; and x is a number which satisfies the valence requirements of the other elements present.

2. The process of claim 1 wherein said hydrocarbons are $C_1$–$C_4$ hydrocarbons.

3. The process of claim 2 wherein said temperatures range from 275° C. to 500° C.

4. The process of claim 3 wherein said temperatures range from 300° C. to 400° C.

5. The process of claim 1 wherein said hydrocarbons are $C_1$–$C_4$ alkanes.

6. The process of claim 5 wherein said carbon monoxide and hydrogen are in a molar ratio of about 1/1.

7. The process of claim 6 wherein essentially no alcohols or acids are produced.

8. The process of claim 1 wherein said catalyst is prepared by the process comprising:
  (a) adding copper-tungstate to a solution containing a decomposable salt selected from thorium and uranium;
  (b) heating such solution to an elevated temperature;
  (c) adding a decomposable salt selected from the alkali or alkaline earth metals to said solution;
  (d) adjusting the pH of said solution to at least 7.5;
  (e) cooling said solution to about room temperature;
  (f) neutralizing said solution;
  (g) recovering the precipitate; and
  (h) calcining said precipitate in the presence of an oxygen-containing gas.

9. Process of claim 8 wherein said elevated temperature in step (b) is between about 80° C. and about 90° C.

10. Process of claim 9 wherein the pH of said solution in step (d) is adjusted to about 9.5.

* * * * *